(12) United States Patent
Harper (10) Patent No.: US 7,107,457 B2
(45) Date of Patent: Sep. 12, 2006

(54) OPTICAL CARD BASED SYSTEM FOR INDIVIDUALIZED TRACKING AND RECORD KEEPING

(75) Inventor: W. Jack Harper, Lakewood, CO (US)

(73) Assignee: BSI2000, Inc., Lakewood, CO (US)

( * ) Notice: Subject to any disclaimer, the term of this patent is extended or adjusted under 35 U.S.C. 154(b) by 0 days.

(21) Appl. No.: 10/726,971

(22) Filed: Dec. 2, 2003

(65) Prior Publication Data

US 2004/0162988 A1 Aug. 19, 2004

Related U.S. Application Data

(63) Continuation-in-part of application No. 09/454,717, filed on Dec. 6, 1999, now Pat. No. 6,775,774.

(51) Int. Cl.
H04K 1/00 (2006.01)
G06F 17/20 (2006.01)
H04L 9/00 (2006.01)

(52) U.S. Cl. ............... 713/182; 713/186; 713/187; 713/193; 713/194; 382/115; 235/386; 235/444; 235/455; 235/462; 235/487; 235/488; 235/490; 235/900; 235/382.5

(58) Field of Classification Search ............ 713/186, 713/187, 193, 194, 1, 2, 100, 150–160, 201, 713/182; 235/386, 444, 455, 462, 487, 488, 235/490, 900, 382.5; 340/5.33, 5.83; 705/1, 705/14, 16, 26, 42, 44, 65, 76; 382/115; 380/229; 709/238–244; 715/866; 714/3; 711/170

See application file for complete search history.

(56) References Cited

U.S. PATENT DOCUMENTS

| | | | |
|---|---|---|---|
| 4,396,914 A | 8/1983 | Aston | 340/5.26 |
| 5,027,401 A * | 6/1991 | Soltesz | 380/54 |
| 5,214,699 A | 5/1993 | Monroe et al. | 713/186 |
| 5,268,963 A | 12/1993 | Monroe et al. | 713/186 |
| 5,412,727 A | 5/1995 | Drexler et al. | 713/186 |
| 5,559,885 A | 9/1996 | Drexler et al. | 235/380 |
| 5,613,012 A * | 3/1997 | Hoffman et al. | 382/115 |
| 5,719,950 A * | 2/1998 | Osten et al. | 382/115 |
| 5,756,978 A * | 5/1998 | Soltesz et al. | 235/380 |
| 5,815,252 A * | 9/1998 | Price-Francis | 356/71 |
| 5,960,403 A | 9/1999 | Brown | 705/2 |
| 6,016,476 A * | 1/2000 | Maes et al. | 705/1 |
| 6,022,315 A | 2/2000 | Iliff | 600/300 |
| 6,031,910 A * | 2/2000 | Deindl et al. | 380/255 |
| 6,266,647 B1 | 7/2001 | Fernandez | 705/14 |
| 6,473,861 B1 | 10/2002 | Stokes | 713/193 |
| 6,999,936 B1 * | 2/2006 | Sehr | 705/5 |
| 2001/0011680 A1 * | 8/2001 | Soltesz et al. | 235/379 |

* cited by examiner

*Primary Examiner*—Taghi T. Arani
(74) *Attorney, Agent, or Firm*—Townsend and Townsend and Crew LLP (57) ABSTRACT

According to the invention, a system for identifying an individual and reading biometric information pertaining to the individual from an optical card is disclosed. The system includes an optical card drive and a biometric scanner that are both coupled to a data processor. The optical card includes biometric data of the individual. The biometric scanner reads the biometric information from the individual. The biometric information is compared with biometric data to assist in authenticating that the individual is associated with the optical card

21 Claims, 5 Drawing Sheets

MedSAPh 2000

Bryan M. Luman
DOB 07/22/1965   Age 33 yrs
Male   Ht. 6'-3"   Wt. 200 lbs.
 Dr. Johnson
 Family Practice
 Blue Cross Blue Shield
 Plan: Blue Choice
 Ply: 123456789   Grp:12432

Complaints: _____________

Treatments: _____________

Physical:
    HEENT   MSK
    NECK     GIO
    CHEST    NEURO
    HEART   MENSTAT
    ARD      EXT Signature: _____________

Vitals / Medications
Trans. _____   B.F. _____
P. _____   R. _____
Medications: _____________

History: _____________

Investigation: _____________

Follow up / Labs: _____________

Codes: _____________

FIG. 3B

ACTIVE
11/11/1999 15:43
BSI2000 Test, 1234
BSI2000, Inc. - President
Jack Harper, 431.02.5582
male age 47 5' 11" 190 lbs
Brown hair Green eyes

DRUG AND ALCOHOL TEST

Tested Clean
DOT 3.14
03/19/1997 First Test
03/25/1999 Last Test

TRAINING

01/30/1996 Welder
02/10/1996 Stainless Vessels
04/12/1998 GMT 2.14
05/13/1998 EMT 23.12
01/12/1998 GDR 2.1
03/11/1997 EDT 3.122
02/19/1997 HDS 4.1
05/30/1998 SKA 3.12
06/10/1997 EDP 9.1
05/30/1998 No Limitations

MEDICAL

05/30/1998 Pulmonary Function Test
                          No Respirator
07/30/1998 Blood Heavy Metal Content Test
02/01/1999 Hearing Loss Test  30% Normal
12/25/1998 Physical Examination
                          Good Health
Rehired & Signed by Garth

5F3CCA01F0A47FBE95CB790C395606F35365100

FIG. 4

OPTICAL CARD BASED SYSTEM FOR INDIVIDUALIZED TRACKING AND RECORD KEEPING

This application claims the benefit of and is a continuation in part of U.S. application Ser. No. 09/454,717 filed on Dec. 6, 1999, now U.S. Pat. No. 6,775,774 which is incorporated by reference in its entirety.

BACKGROUND OF THE INVENTION

This invention generally relates to a system for acquiring and storing information and storing this information in a single portable storage device. More specifically, but not by way of limitation, the system provides a display for displaying identification information carried on the storage device, a biometric identification device, a data processor, and a telecommunications port or communication device.

There are many known devices or systems that allow the identification and tracking of information relating to an individual. A well known example of such systems includes the use of an identification card that includes a photograph and a magnetic machine readable stripe. These systems have gained considerable popularity because of their low cost and ease of use. The limitations of these systems, however, has left important un-met needs in terms of security, reliability and versatility.

More specifically, cards that include an individual's picture or facsimile, suffer from the limitation that the picture can be altered with relative ease. Additionally, the wide use of these systems, which rely on somewhat antiquated printing and reproduction techniques, has made the complete falsification or creation of false identity cards possible for individuals with modest technical training. Thus the problem of identity falsification by way of these systems persists.

Still further, the use of magnetic strips or magnetically encodeable portions in identification systems, relies on cards that are susceptible to inadvertent erasure of the cards by exposure to a strong magnetic field, as may be found on a cashier's counter, a speaker, or other commonly used tools or devices. Thus the reliability or effectiveness of these systems is susceptible to destruction or alteration with common tools or devices.

Still further, magnetically encoded identification cards suffer from the limitation that they can only hold a limited amount of information. Thus, magnetically encoded cards may include identification codes which may be used as a key for comparison with an access code that is manually entered or provided by the user. Thus, these devices can offer only limited identification verification since the amount of information that can be stored as a key is also very limited. This limitation often allows thieves to simply spy on the user as he or she enters the key or verification information to gain access to all of the information needed to duplicate the access card.

BRIEF DESCRIPTION OF THE DRAWINGS

The present invention is described in conjunction with the appended figures.

In the appended figures, similar components and/or features may have the same reference label.

DETAILED DESCRIPTION OF THE PREFERRED EMBODIMENT

The ensuing description provides preferred exemplary embodiment(s) only, and is not intended to limit the scope, applicability or configuration of the invention. Rather, the ensuing description of the preferred exemplary embodiment(s) will provide those skilled in the art with an enabling description for implementing a preferred exemplary embodiment of the invention. It being understood that various changes may be made in the function and arrangement of elements without departing from the spirit and scope of the invention as set forth in the appended claims.

In one embodiment, the present invention provides a system for identifying an individual and reading biometric information pertaining to the individual from an optical card. The system includes an optical card drive and a biometric scanner that are both coupled to a data processor. The optical card includes biometric data of the individual. The biometric scanner reads the biometric information from the individual. The biometric information is compared with biometric data to assist in authenticating that the individual is associated with the optical card.

According to an embodiment of the invention the biometric information or data gathering device includes a fingerprint reading device which collects the image of at least one fingerprint from a hand of the person presenting the optical card. In one embodiment, the optical card contains encrypted information about the fingerprint of the owner or duly authorized user of the card. The fingerprint image information is then used to compare the image with the stored image. The stored image being the image of the authorized user as recorded in the memory of the system. The comparison is carried out by the processor, which executes programs for the operation of the system. A similar comparison process would be carried out in the event that another biometric factor, such as the coloration or pattern on the individual's iris, for example.

Thus, embodiments of the disclosed system will use encrypted computer code or writing to store information on the optical card. The information could pertain to biometric data or could include an image of the individual and/or could include information on the fact that the card had been used to access the system.

Because of the system's data processing and communications capabilities, it is contemplated that the system can be advantageously used for carrying out important identity verification and information storage and transfer processes. One such process or method is a method for employee or personnel tracking. Of particular importance is a system and method for implementing substance abuse or drug use programs at a facility. With this system and method it is contemplated that the optical card of the disclosed system would be used to store, in an encrypted manner, information pertaining to the identity of the cardholder 4 as well as certain risk characteristics about the individual 4 and the area that is to be accessed.

The risk characteristics will be factors about the individual which will allow the system to determine a proper statistically derived frequency or model of random testing.

For example, if the individual is of a high risk characteristic, either because of the job to be performed by that individual or because of the individual's personal history, then the system would select the proper statistical model to produce an adequate random determination for whether this individual should report to a drug testing facility for testing or continue through to work area.

Thus, to properly secure areas and administer the appropriate drug testing program, the optical card could also store information on the cardholder's training, health, emergency assistance precautions or special needs in case of emergency.

Still further, it is contemplated that the disclosed system be used in conjunction with other data input devices, such as a bar code scanner. It is further contemplated that when used with a scanner type input device, the system may be used for the input and tracking of medical records of the individual cardholder 4 or owner. In this embodiment, the optical card would be used to carry a combination of scanned image information, typed or manually entered information, and information by code scanning.

In this embodiment, the information obtained by code scanning is standard or commonly used terms or codes such as CPT codes, treatments, and observations used during the examination of patients. The scanned image storage capabilities of the optical card can be used to store the examining physician's notes, which is entered onto the card by way of the code scanner in one embodiment. For example, when a cardholder 4 arrives at a physician's office, the physician would use the disclosed system to access the medical records as encoded on the optical card. These records would be accessed from the optical card and displayed by the system on a screen or printed out by exporting the information from the disclosed system to a printer. Once the physician examines the patient, the physician writes down his or her observations and prescriptions in a customary, well known manner.

The physician's notes are then read by an assistant or data entry operator. The data entry operator transcribes these notes by using standardized comments or inputs as presented as a part of a series of bar codes, each bar code representing a commonly used term or observation in that area of medicine. Additionally, the actual notes or comments hand written by the physician are then scanned and the image recorded on the optical card along with the transcribed notes. This combination of transcribed notes and images will ensure accurate retrieval of the records, and provide the physician with a way to authenticate and certify that the records were his or her notes.

The use of the optical card and system disclosed herein allows the owner of the card, or card carrier, to carry a single card with a large amount of information pertaining to that individual's identity and medical history so as to allow anyone with the disclosed system to access the information and decide on the appropriate course of treatment.

It will be appreciated that embodiments of the disclosed system are a particularly versatile tool in that they can be used for a variety of tasks that identify an individual. Also, embodiments of the system can help satisfy the need to carry out data processing operations which pertain specifically to the individual identified by the card.

Still further, it will be appreciated that embodiments the disclosed invention provide a versatile system and method for implementing employee monitoring programs and programs designed for testing employees for substance abuse.

Figure 1:
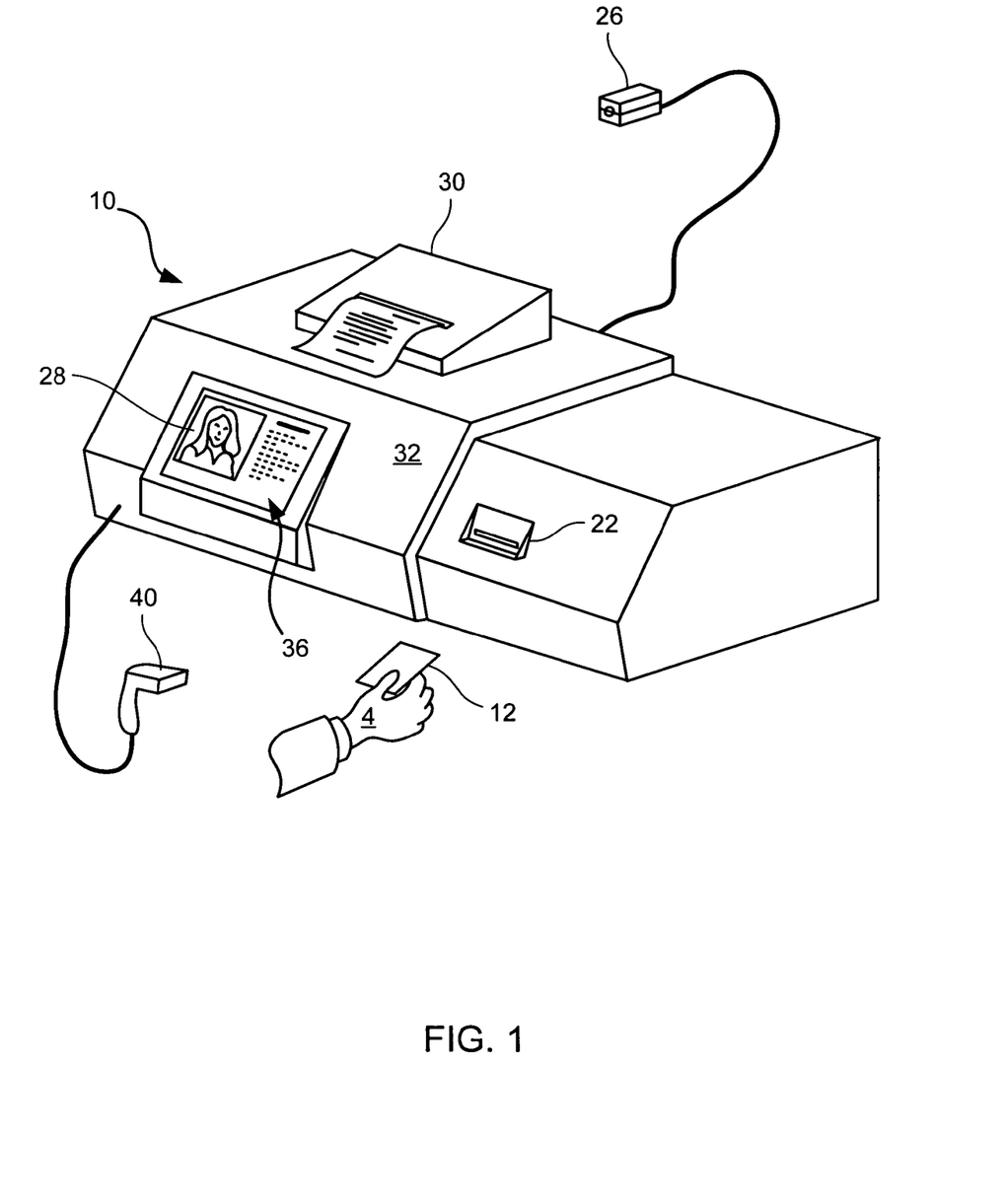
FIG. 1 is a perspective view of an embodiment of the invention, the view also illustrating the use with the addition of a barcode scanner.

Turning now to FIG. 1 where a self-contained system 10, made in accordance with the principles taught herein, is illustrated. The system 10 is useful for identifying and storing information pertaining to an individual 4. According to one embodiment of the invention, the system 10 uses an optical card 12 for storing the information pertaining to the individual 4. It is contemplated that this information pertaining to the individual 4 may include information about the individual's health; or physical characteristics; audit trail information that logs the fact that the system 10 and the optical card 12 were used together; and/or other data which is useful in carrying out calculations, such as statistical calculations pertaining to the individual 4, within the system 10. In some embodiments, the optical card is rectangular in shape, like a credit card, but in others it is disk-shaped and may or may not be housed in a protective cover.

In this embodiment, the optical card 12 includes well known write once, read many (WORM) type of the category or class of media discussed in U.S. Pat. No. 5,579,772. State of the art optical cards are capable of storing up to four megabytes of digital information. This translates into approximately 1500 type-written pages. Thus, it is contemplated that state of the art optical cards are particularly well suited for use with the disclosed system 10. However, it is important to note that the principles taught herein are applicable to other highly transportable WORM-type devices.

The system 10 will serve as a portable, self-contained unit, that does not depend on a connection or data link to a larger data holding-and processing unit. Thus, the user can simply place one of the systems 10 at a desired location in an office building, manufacturing plant, laboratory, and so on, and carry out all of the necessary identity verification and program implementation without having to establish communications with a central data processing center. The system 10 uses the data storage capabilities of the optical card 12 to store information such as photographs in a digital format, program parameters such as number of times that the optical card has been presented to the system 10, information about the cardholder 4 who is being tracked or identified by the system 10, this information may include medical history, substance abuse history, job access requirements and/or authority to enter secured areas.

Figure 2:
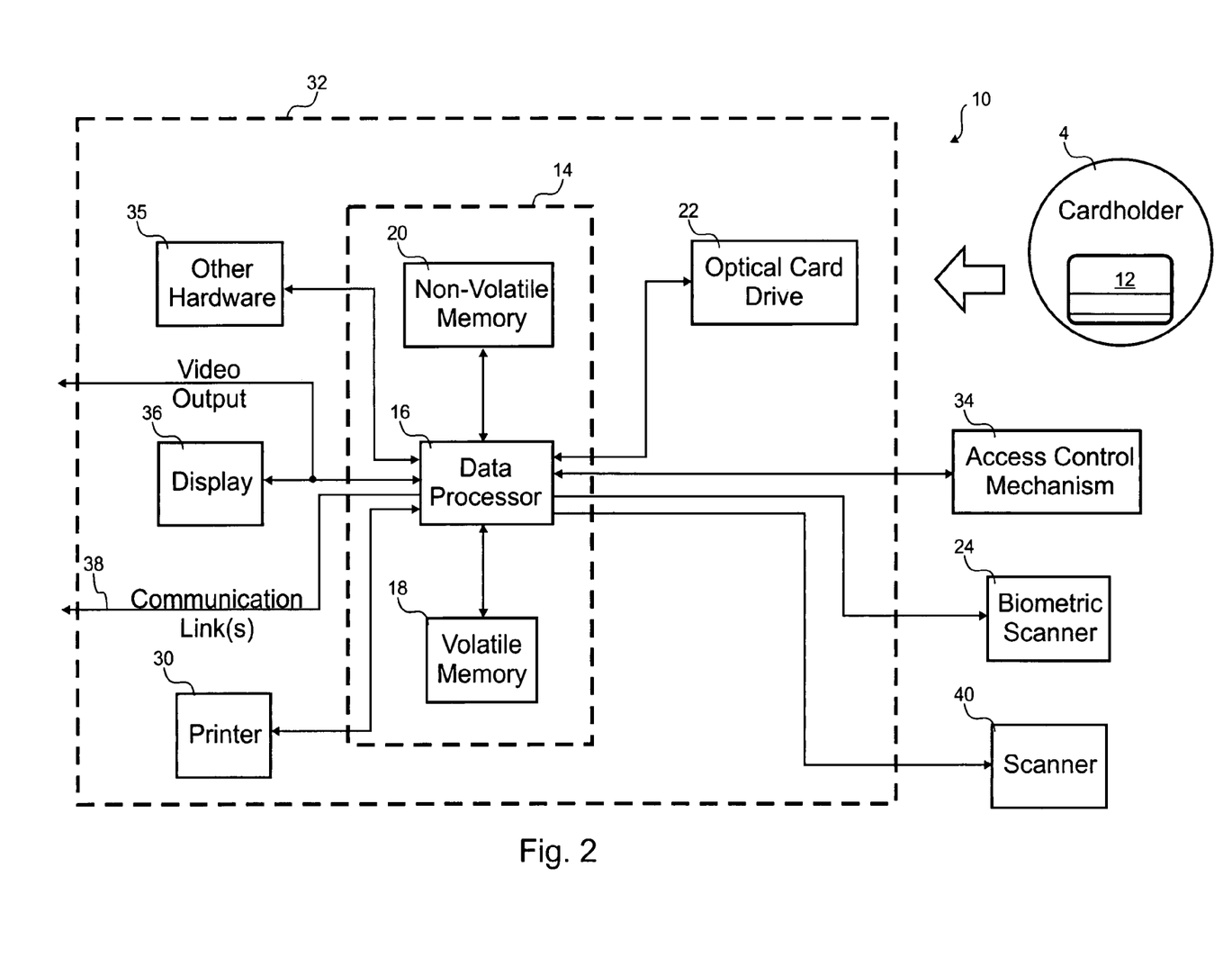
FIG. 2 is a schematic of the architecture of an embodiment of the invention.

Thus, as shown on FIG. 2, it is contemplated that the system 10 will include data processor and store 14, which in one embodiment will include a data processor 16 (e.g., an INTEL™ x86 series type of processor), non-volatile memory 20 (e.g., hard disc drive, flash memory, battery-backed RAM, magnetic RAM, etc.) and volatile memory 18 (e.g., SRAM, RAM, etc.). The non-volatile memory 20 stores a basic input and output system processing and access disk software (e.g., MICROSOFT™ Windows or LNUX™).

Also shown on FIG. 2 is an optical card drive 22, which serves for reading data from the optical card 12 and writing data on to the optical card 12. In an embodiment of the invention, this optical card drive 22 is an optical card read/write apparatus manufactured and sold by the DREXLER TECHNOLOGY CORPORATION™ of Mountain View, Calif. The optical card drive 22 is in communication with the data processor 16. The term "communication" as used herein means that data can be transferred from one device to the other. This data transfer may be carried out through radio waves, optical signals, electrical pulses, or other ways for allowing data transfer between two devices.

Information that has been stored on the optical card 12, by way of a strong encryption method, is retrieved into the data processor 16. This information includes a digitized photograph 28 of the cardholder 4; biometric identification information; information about the cardholder's history, such as substance abuse and testing, training and qualifications;

important medical limitations and emergency treatment information; and executable program information. The executable program information is a program that is downloaded from the card onto the data processor and store 14 where it is executed. In one embodiment of the invention, this executable program is a drug testing program which suits the needs of a particular entity which is using the system 10. The drug testing program is executed by the data processor 16, which also used information retrieval from the optical card 12 as the data on which to carry out its operations.

An embodiment of the invention is shown on FIG. 2 that includes a biometric scanner 24 for obtaining biometric data from an individual 4. According to an example of the invention, the biometric scanner 24 for obtaining biometric data from an individual 4 includes a fingerprint reading device such as the fingerprint scanner sold under the product name BIOMOUSE PLUS™ by the AMERICAN BIOMETRICS COMPANY™ of Ottawa, Canada, but other fingerprint or biometric scanners could be use. It is important to note that while this example of the invention uses a fingerprint scanner, it is also contemplated that other biometric scanning or reading devices may be employed with the system, such as iris pattern scanning, hand geometry, voice recognition, face recognition, or even DNA recognition devices.

The information generated by the biometric scanner 24 is then transferred to the data processor and store 14 where it is compared with a verified pattern stored on the optical card 12 to positively identify that the true cardholder 4 is present before the system 10. The biometric information on the optical card 12 is verified at the time it is written to the card such that later comparisons have a verified baseline measurement. Authorized agents, such as police departments and motor vehicle offices, could be used assure accurate biometric information is written to the card 12.

Once the verification of identity has been completed, the system 10 uses the executable program from the optical card 12 to implement the drug testing, record keeping, banking, or other programs, such as government assistance programs where funds are to be used by recipients for the purchase of specific items. The system 10 will then proceed to carry out the operations of the programmed task as controlled by the data and code encrypted on the optical card 12. The system 10 then communicates with the cardholder 4 by way of a video output for an external display or an integral display 36, which shows the cardholder's picture 28 and instructions about the access or transaction procedures. Additionally, it is contemplated that the system 10 will include a printer 30 in some embodiments that is used to provide the cardholder 4 with a printed record of instructions or details about the interaction between the cardholder and the system 10. The printer 30 in this embodiment is integral with the housing 32, but could be externally located in other embodiments.

In an embodiment of the invention, the system 10 is self-contained in that the display 36, such as a liquid crystal display (LCD) or other display screen; the data processor and store 14; and the optical card drive 22 are all held by the same housing 32. It is contemplated that the biometric scanner 24 for obtaining biometric data is connected to the housing 32 by way of a cable or other wired or wireless communication mechanism. However, it is contemplated that in furtherance of providing the benefits of a stand-alone system, the biometric scanner 24 for obtaining biometric data may be attached or fixed to the housing. In some embodiments, certain components could be detached for various applications, for example, the display screen 36 may be removable and replaced by a larger display 36 coupled to the housing 32 with a cable or wireless connection.

The display 36 can be used to display instructions to the cardholder 4 or someone else using the system 10. For example, the display could present an image of the cardholder 4. An attendant could compare that image with the cardholder's appearance to authenticate that the optical card 12 belongs to the cardholder 4. The comparison of the image to the cardholder appearance could be automatic in other embodiments. The biometric scanner 24 could be a camera. An acquired image could be compared with the retrieved image by the data processor and store 14 using face recognition technology. Similar automated authentication is possible with fingerprint, iris, voice, hand geometry comparisons.

The software that performs the biometric comparison could be stored on the optical card 12 and/or the non-volatile memory 20. The system could include an initial version of the biometric comparison software. If an optical card 12 were presented with updated biometric comparison software, it could replace the version stored on the non-volatile memory 20. In this manner, field-upgrades of the software is performed.

This embodiment of the disclosed system 10 offers important new and useful results in that it allows an entity to operate many systems 10 at various locations, without having to have the systems 10 networked together. The encryption and record keeping of transactions is all carried out by the each system 10 and recorded in an encrypted fashion on the optical card 12. Thus in going from location to location, the cardholder 4 will be received and handled as if the system 10 were part of a larger network connected computers, without a persistent network connection.

It is also contemplated that the system 10 may optionally include a keypad or other data input device, such as a voice activated input device, to allow a user to enter instructions, passwords or the like into the system 10. It is also contemplated that the system 10 may include a relay or other output signal that can control an access control lock 34 for opening, closing and/or locking a doorway, gate, safe, or other controlled space or piece of equipment. Additionally, it is also important to note that it is contemplated that the system 10 could be connected to a telecommunications system, network or other data transfer system for transferring data to a central system or to another device. Adding a connection to a central system could provide the provision of a data backup system option to the disclosed invention or could allow software or firmware updates. Some embodiments use the optical cards to provide information to the various self-contained systems for data backup and system updates, for example, the optical card could include software that could update the firmware or software in the system 10 if it were determined out of date.

As an example of the system 10 in use in air transport industry, the system 10 is used to control access to an aircraft maintenance work area. In this example, access to the secured work area is locked by a magnetic door lock 34 that is controlled by the system 10. A card holding mechanic, who is about to enter the work area, approaches the system 10 and inserts the optical card 12 into the system 10 and places at least one finger on the biometric scanner 24 to read the fingerprint. When the optical card 12 is inserted into the optical card drive 22, an executable program is downloaded and executed by the data processor and store 14 to allow the system 10 to compare biometric data obtained from the mechanic against an authenticated scan(s) on the optical card 12. The picture 28 of the individual 4 is also read from the optical card 12 and presented on the display 36. The image 28 on the screen 36 can be viewed by a security guard at the gate to further authenticate the mechanic's identity. If the comparison of the biometric information results in a positive identification, then the system 10 could initiate other software routines that can originate from the optical card 12 itself or may have been previously loaded on the data processor and store 14.

Figure 4:
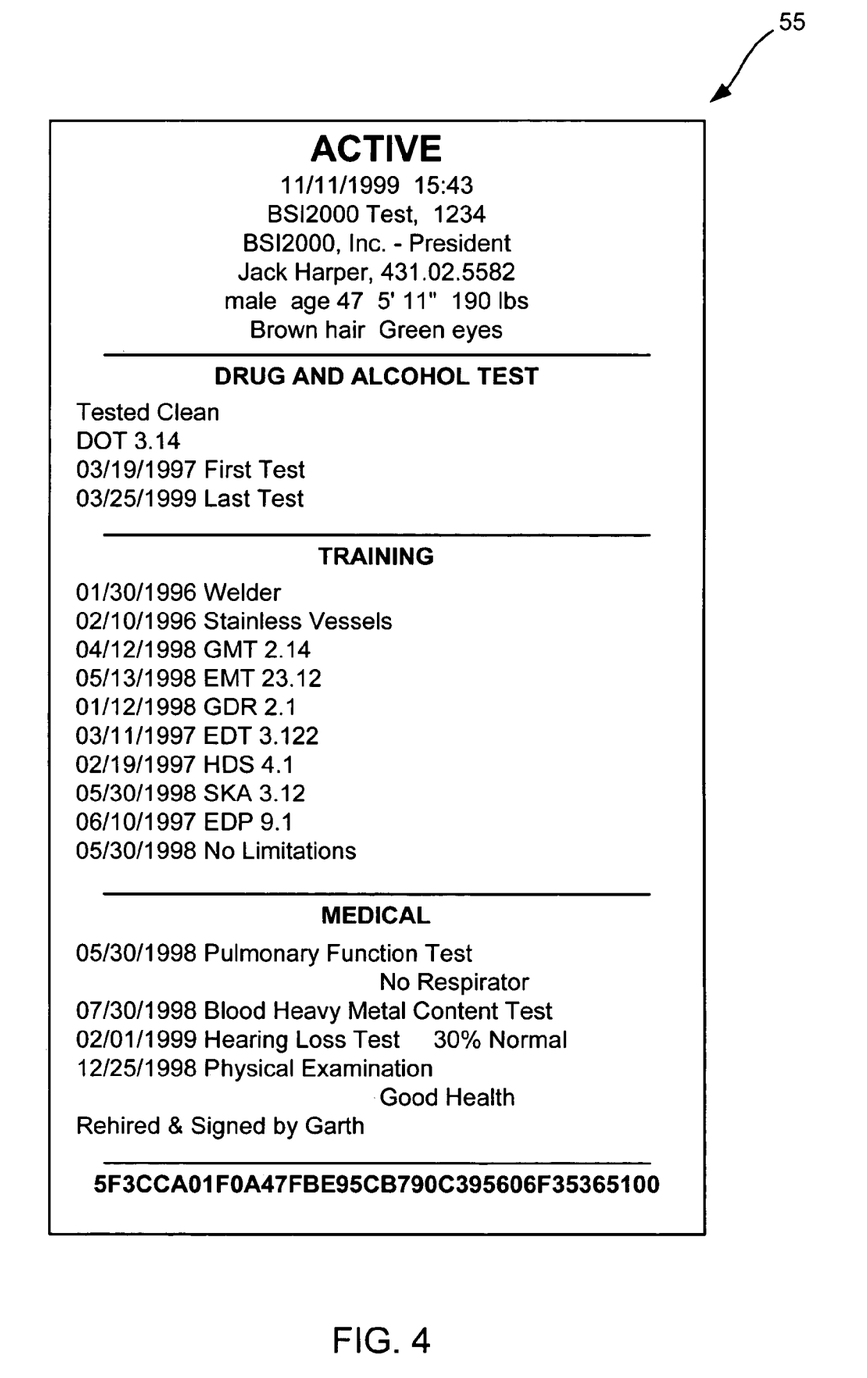
FIG. 4 is an example of a printout of information or instructions provided by the system.

In one example, a drug testing program could be initiated as part of a random or periodic screening regiment or one controlled by an algorithm run with a program on the optical card 12. This program would weigh the sensitivity of the individual's duties, any drug test history and any medical history and run a random number or selection generation program to indicate whether this individual 4 should be tested for controlled substances. Of course, other parameters than those enumerated above may be used in the algorithm. If the individual 4 is selected for drug testing, the system 10 would communicate to the individual 4 by way of the display 36 and or by printing out a summary with the printer 30. An example printout 55 is shown on FIG. 4. This printout 55 could include the time and place where the individual 4 is to report for drug testing and other instructions pertinent to the current situation. Audit information about the requirement that the test be carried out would immediately, for example, is written in encrypted form on the optical card 12 by the optical card drive 22. Any further use of the optical card 12 could revisit compliance by determining if the drug test requirement was satisfied by checking the records held by the optical card 12.

Referring once again to FIG. 2, as discussed above, it is contemplated that the system 10 may also include communication link 38 that may be used to instantaneously warn or inform a supervisor or other responsible individual of the test requirement, and thus the responsible individual may immediately escort the employee to the drug test facility. This escort would minimize the possibility of any attempt to alter the drug test by ingesting large amounts of water or other dilutants, for example. Additionally, it would minimize the opportunity of obtaining a phony sample from a known drug-free individual or otherwise foil the test. The communication link could be ethernet, serial, parallel, USB, firewire, wireless, infra red, etc.

Still another embodiment of the system 10 optionally includes the use of a barcode or RFID scanner 40 for entering information into the system 10. The scanner 40 would be in communication with the data processor and store 14 to allow the information entered into the system by way of the scanner 40.

Although not delineated in FIG. 2, there is other hardware 35 in the system 10. For example, a power supply is included that may be partially inside and/or partially outside the enclosure 32. There could be an interface to an integral or external to a removable or non-removable storage drive. Some embodiments could include a modem, ethernet or other networking port. Some embodiments could have status lights and/or LEDs, display panels, control panels, speaker, microphone, etc. For future expansion, some embodiments could have an expansion bus where circuit card could mate to allow future upgradability.

Figure 3A:
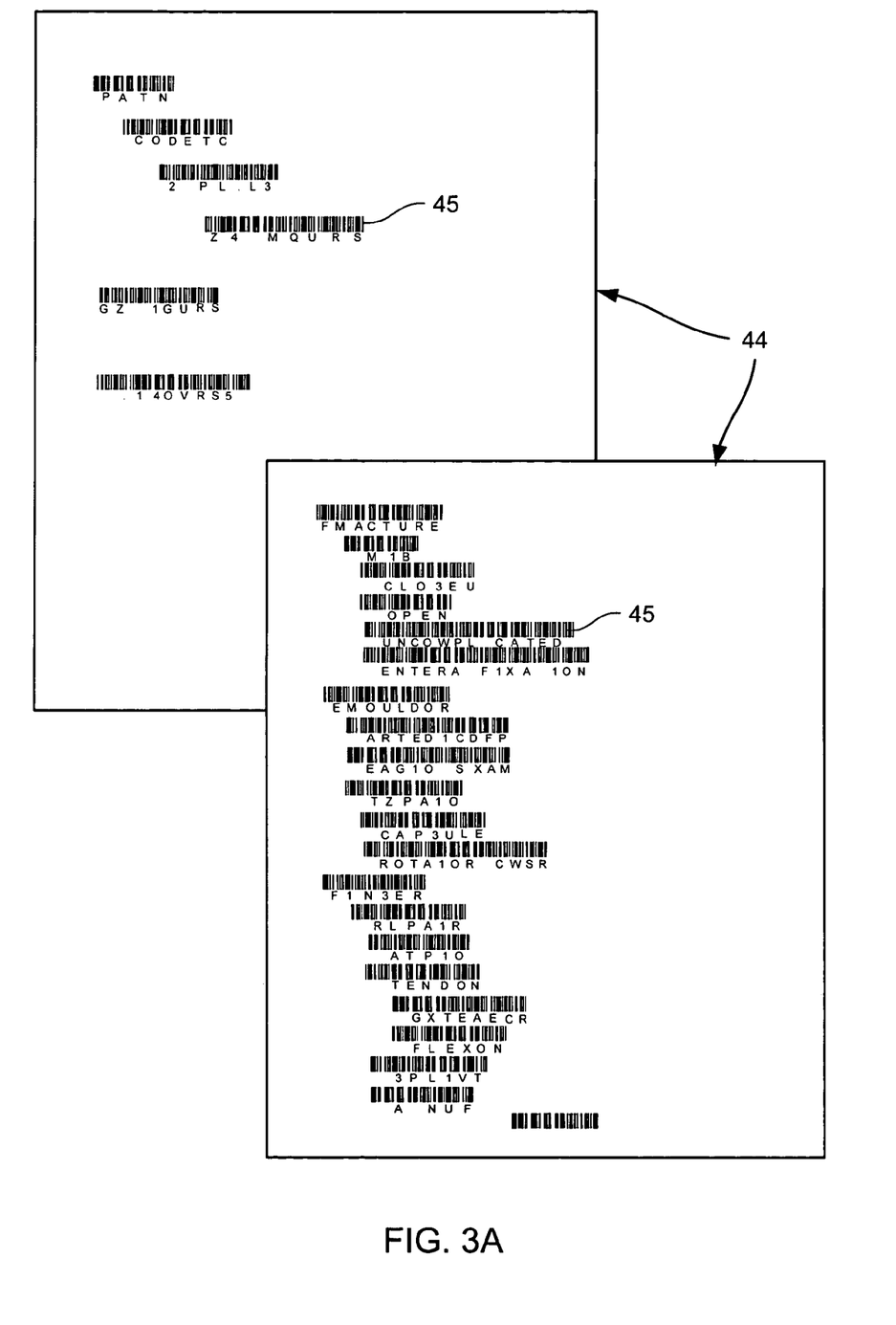
FIG. 3A illustrates an embodiment of a barcode form to input information into the system.
Figure 3B:
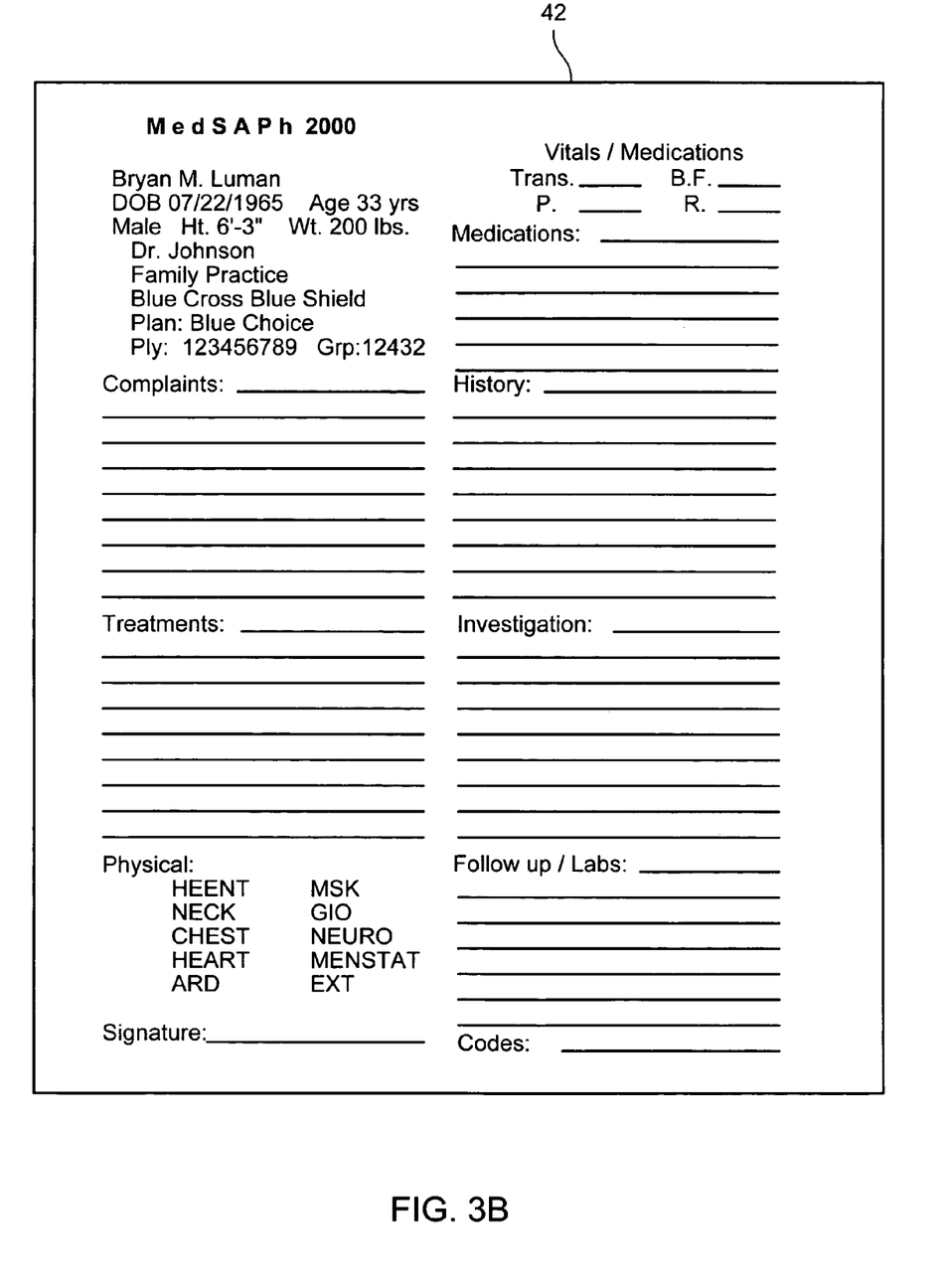
FIG. 3B illustrates an embodiment of physician's notes for input into the system.

Referring now to FIGS. 1–3B, and particularly FIGS. 3A and 3B, it will be understood that the addition of the barcode scanner 40 would allow the user to further harness the versatility of the disclosed system 10. In this embodiment, the system 10 is used for storage and retrieval of medical records. In use, a cardholder 4 would arrive at a physician's office with his or her medical records stored as encrypted data on the optical card 12. The physician would then access the medical records by inserting the optical card 12 into the optical card drive 22 and have the patient place a finger on the biometric scanner 24 for obtaining biometric data from the patient. The system 10 would compare the measured and stored biometric information. The physician observes the display 36 to determine whether the patient presenting the card appears the same as the image 28 depicted on the display 36. An additional benefit to including the image information on the optical card is that the physician may look at the image 28 on the display 36 and compare that image with the patient's current appearance. Any changes in the appearance of the patient may aid the physician in the diagnosis of the patient.

Once the physician has retrieved the records stored on the optical card 12, and examined the patient, the physician may then write down or enter recommendations and other observations. An example of the physician's notes 42 is shown in FIG. 3B. Of course, the physician may even take photographs, other types of diagnostic imaging and/or medical tests of the patient for storage in a digital format in the optical card 12. This medical information may be used at a later time for further evaluation of the patient's progress.

The physician's notes 42 may also be stored in the optical card 12. These notes can be stored in two forms, more specifically, as digitized scans or as digital text characters. The digitized scan would be a scanned facsimile that could be later retrieved from the optical card 12 for display 36 and/or printout 30. With images, such as the photographs or scanned notes, they serve a purpose in that they may be retrieved at a later date and aid the physician in refreshing memory about the patient's visit or could be used by another medical professional.

Since the diagnosis and observations about the patient's condition are likely to include many typical or commonly found observations. These comments or observations can be entered into the system 10 for inclusion on the optical card 12, reporting to a remote data storage point and/or printout with the printer 30. An example barcode printout 44 with various barcodes 45 on two sheets is shown in FIG. 3A. The physician's notes are, at least in part, found as terms or codes associated with the various barcodes 45 on the barcode printout 44 shown in FIG. 3A. The various barcodes 45 could be in any machine readable format, for example, a one-dimensional, a two-dimensional bar code or other machine readable code.

As mentioned above, FIG. 3A shows barcode form sheets 44 having various barcodes 45 corresponding to a selection of notes that a physician might make during an office visit. The barcode form sheets 44 could be produced by a program on the optical card 12 and produced on the printer 30. The barcodes 45 printed could only be those relevant to a particular stage of treatment for the patient. During the patient's visit, the physician's notes are indicated by a circle or other mark to indicate which bar codes 45 are appropriate for the patient. Textual notes could be included on the forms 44 that explain or remind the physician of the meaning of the various barcodes 45.

The indicated barcodes 45 can be easily entered into the system 10. In one embodiment, a physician's assistant uses the barcode scanner 40 to transcribe the physicians's notes into computer readable text that is also stored as encrypted data on the optical card 12. A circle in this example is used to show the assistant the relevant barcodes 45 to scan on the barcode form 44. The corresponding codes or notes are encrypted into the patient's optical card 12 after entry. The relevant barcodes 45 or scanned notes 42 can be printed at a later time and/or subsequent visit.

The codes and text written to the optical card 12 may include a prescription or other therapy for the patient. The patient may then got to a pharmacy which provides the needed prescriptions and that also posses a system 10. The optical card 12 and the system 10 are then used to verify the identity of the patient and to retrieve the prescriptions to be filled. The records of the transactions may then also be encripted onto the card. It is important to note that the encryption and data retrieval system and the programmability of the data processor and store 14 used to with the system 10 may be used to allow selective access to the records stored in the optical card 12. Thus the pharmacy would only be able to retrieve identification information, the prescriptions and/or other specified information while other information is not available to the pharmacy.

In still another variation of the use of the disclosed system 10, a method for tracking and controlling the inventory of work place tools, equipment, classified documents, or controlled items is disclosed. With this method, a tool crib or materials distribution center would maintain an inventory of tools or materials to be distributed to employees. These tools or materials would be inventoried by way of a barcode attached to the tool or material to be assigned to an employee.

When the employee desires to obtain a tool or material, he or she will visit the tool crib or distribution center with the optical card 12. The tool crib or distribution center has a system 10, which would be used, as described above, to identify the individual cardholder 4. The system 10 would then access information stored in the card 12. In one embodiment, this information would include information about tools or materials that have been checked out by the cardholder 4, employee. For example, if the employee is a nurse that is authorized to administer certain kinds of medication, this authority would be encripted on to the optical card 12. The system 10 would then use the information from the optical card 12 to provide authorization to check out the equipment, material or medications requested by the nurse. Once authorized, the cardholder 4 would receive the materials from the tool or materials dispensing area.

To inventory the release of these tools or materials, the person issuing the tools or materials would use the barcode or RFID scanner 40 to record the fact that these materials were issued to the cardholder 4. Of course, it is contemplated that a double entry type system may be used, where a computer connected to the system 10 would deduct the materials form an inventory stored in its memory in addition to recording the transaction on the optical card 12. The disclosed system 10 would be used to record the event on the cardholder's optical card 12 to create an audit trail. Additionally, the system 10 would also be used to record the return of tools or materials on the optical card 12.

By recording the fact that tools or other supplies have been assigned to the cardholder 4, the system 10 can be used to control inventories of the tools by combining the use of the information recorded on the optical card 12 to control the ingress and egress to the work area. Thus the cardholder 4 would check out a tool from a tool crib within the secured area, the fact that the tool was checked out to the cardholder 4 would be recorded on the cardholder's optical card 12. The cardholder 4 would then use the tool to carry out his or her duties throughout the work day. At the end of the work day the cardholder 4 would insert the optical card 12 into the system 10 that controls access to the work area. By inserting the card into the system 10, the system 10 would read from the card the fact that a tool was checked out by that cardholder 4. If the tool has not been returned to the tool crib, the system 10 controlling access to the work area would not allow the person to leave until the tool was returned to the tool crib and the system 10 located at the tool crib used to record the return on the card 12.

Of course, it is contemplated that systems for allowing the override of the access control in case of fire or other emergencies may be incorporated into the system without departing from the scope of the disclosed invention. Further, some embodiments could include self-contained systems 10 that could communicate with other equipment or a central location in real-time or periodically. There could be some systems 10 with network access, some with periodic network access and still others with no network access in a given deployment.

While the principles of the invention have been described above in connection with specific apparatuses and methods, it is to be clearly understood that this description is made only by way of example and not as limitation on the scope of the invention.

What is claimed is:

1. A system for identifying an individual and reading biometric information pertaining to the individual from an optical card, the system comprising:
   an optical card drive adapted for reading from and writing to the optical card, wherein the optical card includes biometric data of the individual;
   a biometric scanner that reads the biometric information from the individual;
   a data processor coupled to the optical card drive and the biometric scanner, wherein the biometric information is compared with biometric data to assist in authenticating that the individual is associated with the optical card; and
   an access control mechanism, whereby the access control mechanism is manipulated on verification of an identity of the individual.

2. The system for identifying the individual and reading biometric information pertaining to the individual from the optical card as recited in claim 1, further comprising a display for displaying an image retrieved from the optical card, whereby the image of the individual can be compared to the individual.

3. The system for identifying the individual and reading biometric information pertaining to the individual from the optical card as recited in claim 1, wherein the data processor is programmed for encrypting and deciphering encrypted data obtained from the optical card drive.

4. The system for identifying the individual and reading biometric information pertaining to the individual from the optical card as recited in claim 1, wherein the optical card drive, the biometric scanner, and the data processor are held in a single housing.

5. The system for identifying the individual and reading biometric information pertaining to the individual from the optical card as recited in claim 1, further comprising a barcode scanner coupled to the data processor.

6. The system for identifying the individual and reading biometric information pertaining to the individual from the optical card as recited in claim 1, further comprising a communication link for sending and receiving data of the system.

7. A system for identifying an individual and reading biometric information pertaining to the individual from an optical card, the system comprising:

an optical card drive adapted for reading an image of the individual from the optical card;

a display for displaying the image retrieved from the optical card;

a data processor coupled to the optical card drive and the display, wherein the image of the individual is displayed while the individual's appearance is automatically compared to the image to assist in authenticating that the individual is associated with the optical card; and an access control mechanism, whereby the access control mechanism is manipulated on verification of and identity of the individual.

8. The system for identifying the individual and reading biometric information pertaining to the individual from the optical card as recited in claim 7, further comprising a biometric scanner that reads the biometric information from the individual, wherein:

the optical card includes biometric data of the individual, and the biometric information is compared with biometric data to assist in authenticating that the individual is associated with the optical card.

9. The system for identifying the individual and reading biometric information pertaining to the individual from the optical card as recited in claim 7, wherein the optical card drive, the display, and the data processor are held in a single housing.

10. A system for identifying an individual and reading biometric information pertaining to the individual from an optical card, the system comprising:

a biometric scanner for obtaining biometric data from the individual;

a housing comprising:

an optical card drive adapted for reading from and writing to the optical card, and a data processor coupled with the optical card drive and the biometric scanner, wherein the data processor assists in comparing data from said optical card and the biometric data and delivers data to the optical card drive for writing on the optical card and wherein audit information is written to the optical card during interaction with the system; and a video output for displaying an image corresponding the individual, wherein the image is read from the optical card.

11. The system for identifying the individual and reading biometric information pertaining to the individual from the optical card as recited in claim 10, wherein the optical card stores a prescription or other medical therapy.

12. The system for identifying the individual and reading biometric information pertaining to the individual from the optical card as recited in claim 10, wherein data processor is programmed for assigning testing of the individual with a reading of the optical card.

13. The system for identifying the individual and reading biometric information pertaining to the individual from the optical card as recited in claim 10, wherein the optical card includes software for interpreting information stored on the optical card.

14. The system for identifying the individual and reading biometric information pertaining to the individual from the optical card as recited in claim 10, wherein the housing further comprises a printer that is coupled to the data processor.

15. The system for identifying the individual and reading biometric information pertaining to the individual from the optical card as recited in claim 10, wherein the biometric scanner comprises at least one of a fingerprint reader, an iris reader, hand geometry reader, voice recognition device, face recognition device, and a DNA recognition device.

16. The system for identifying the individual and reading biometric information pertaining to the individual from the optical card as recited in claim 10, wherein the optical card is disk-shaped.

17. A method for tracking an individual and information about the individual, the method comprising:

assigning an optical card to the individual;

reading first biometric information from the optical card;

gathering second biometric information from the individual;

comparing first biometric information and the second biometric information, wherein the reading, gathering and comparing steps are automatically performed with a system that includes a optical card drive, a biometric scanner and a data processor;

authenticating an identity of the individual based upon, at least, the comparing step;

assigning a test of the individual based on the identification; and writing information to the optical card indicating the test was assigned.

18. The method for tracking the individual and information about the individual as recited in claim 17, further comprising steps of:

providing a display for displaying data from the data processor;

reading an image from the optical card;

displaying the image on the display, whereby an attendant can compare the image with the individual to authenticate that the optical card is associated with the individual.

19. The method for tracking the individual and information about the individual as recited in claim 17, further comprising a step of writing information to the optical card with the optical card drive that relates to the authenticating step, whereby the information provides part of an audit trail for later inspection.

20. The method for tracking the individual and information about the individual as recited in claim 17, further comprising a step of encrypting information that is written on the optical card.

21. The method for tracking the individual and information about the individual as recited in claim 17, further comprising a step of writing a digitized image of a document to the optical card.

* * * * *